(12) United States Patent
Shen et al.

(10) Patent No.: US 8,168,437 B2
(45) Date of Patent: May 1, 2012

(54) QUANTITATIVE DETERMINATION OF RISEDRONATE IN URINE BY SPE-LC-MS-MS

(75) Inventors: Liduo Shen, Easton, PA (US); Yongyi Luo, Doylestown, PA (US)

(73) Assignee: Sanofi-Aventis U.S. LLC, Bridgewater, NJ (US)

( * ) Notice: Subject to any disclaimer, the term of this patent is extended or adjusted under 35 U.S.C. 154(b) by 0 days.

(21) Appl. No.: 12/554,111

(22) Filed: Sep. 4, 2009

(65) Prior Publication Data

US 2009/0320572 A1    Dec. 31, 2009

Related U.S. Application Data

(63) Continuation of application No. PCT/US2008/055849, filed on Mar. 5, 2008.

(60) Provisional application No. 60/893,444, filed on Mar. 7, 2007.

(51) Int. Cl.
*G01N 30/84* (2006.01)

(52) U.S. Cl. ...... 436/105; 436/103; 73/61.55; 73/61.52; 73/61.41; 73/53.01

(58) Field of Classification Search .................. 436/105, 436/103; 73/61.55, 61.52, 61.43, 61.41, 73/53.01
See application file for complete search history.

(56) References Cited

FOREIGN PATENT DOCUMENTS
WO    WO 2006/127973    11/2006

OTHER PUBLICATIONS

Cantrill, J. A., et al., Low Dose Intravenous 3-Amino-1-Hydroxypropylidene-1, 1-Bisphosphonats (APD) for the Treatment of Paget's Disease of Bone, Ann. Rheumatol. Dis., (1986), vol. 45, pp. 1012-1018.
Chester, T. L., et. al., Dual Flame Photmetric Phosphorus-Selective Detector for High Performance Liquid Chromatography, Anal. Chem., (1980), vol. 52, pp. 1621-1624.
Elomaa, I., et. al., 47 Kd Antigen of Candida Albicans, Lancet, (1985), i:, pp. 1155.
Kosonen, J. P., et. al., Determination of Disodium Clodronate in Bulk Material and Pharmaceuticals by Ion Chromatography With Post-Column Derivatization, Journal of Pharmaceutical & Biomedical Analysis, vol. 10, No. 10-12, pp. 881-887, (1992).
Lovdahl, M. J., et al., Anion-Exchange Separation and Determination of Bisphosphonates and Related Analytes by Post-Column Indirect Fluorescence Detection, Journal of Chromatography A, vol. 850, pp. 143-152, (1999).
Meek, S. E., et. al., Liquid Chromatographic Separation of Phosphorus Oxo Acids and Other Anions With Postcolumn Indirect Fluorescence Detection by Aluminum-Morin, Anal. Chem., (1988), vol. 60, pp. 1397-1400.
Mitchell, D. Y., et. al., Risedronate Gastrointestinal Absorption is independent of Site and Rate of Administration, Pharmaceutical Research, vol. 15, No. 2, (1998).
Niemi, R., et. al., Simultaneous Determination of Clodronate and Its Partial Ester Derivatives by Ion-Paris Reversed-Phase High-Performance Liquid Chromatography Coupled With Evaporative Light-Scattering Detection, Journal of Chromatography B, vol. 701, (1997), pp. 97-102.
Turcotte, S., et al., Sensitive Assay of Risedronic Acid in Human EDTA K3 Plasma Using LC/MS/MS, AAPS Pharmsci, Abstract, (2003), vol. 5, No. 4, pp. M1357.
Vallano, P.T., et. al., Determination of Risedronate in Human Urine by Column-Switching Ion-Pair High Performance Liquid Chromatography With Ultraviolet Detection, Journal of Chromatography B, vol. 794, pp. 23-33, (2003).
Virtanen, V., et. al., High-Performance Liquid Chromatographic Method for Simultaneous Determination of Clodronate and Some Clodronate Esters, Journal of Chromatography, vol. 617, pp. 291-298, (1993).
Zhu, L. S., et. al., A General Approach for the Quantitative Analysis at Bisphosphonates in Human Serum and Urine by High-Performance Liquid Chromatography/Tandem Mass Spectrometry, Rapid Communications in Mass Spectrometry, vol. 20, pp. 3421-3426, (2006).
Oasis™ Sample Extraction Products, (Online), (1989), pp. 1-10, Retrieved from the Internet: URL:HTTP//WWW.WOONGKI.COM/PRODUCT/SAMPLE_HANDLING/EXTRACTIONS/HLB.PDF.

*Primary Examiner* — Christine T Mui
(74) *Attorney, Agent, or Firm* — Serena Farquharson-Torres; Scully, Scott, Murphy & Presser, P.C.

(57) ABSTRACT

The disclosure provides a method for quantitatively determining risedronate in a urine sample by adding an internal standard to the urine sample, applying the urine sample to a polymeric water-wettable reverse-phased sorbent preconditioned with methanol, washing the sorbent with TEA in water and formic acid in methanol, eluting risedronate with a mixture of methanol and water containing EDTA under vacuum, evaporating the eluted solution and reconstituting with a mixture of methanol and $NH_4OH$ buffer and analyzing the sample with a LC-MS/MS system.

2 Claims, 6 Drawing Sheets

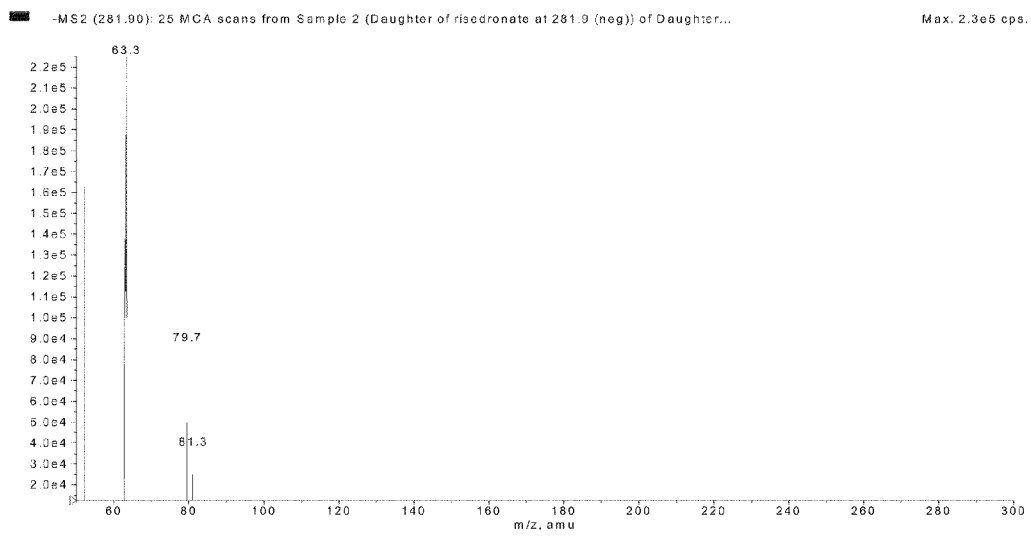
FIGURE 1. ESI-MS Spectrum of Risedronate

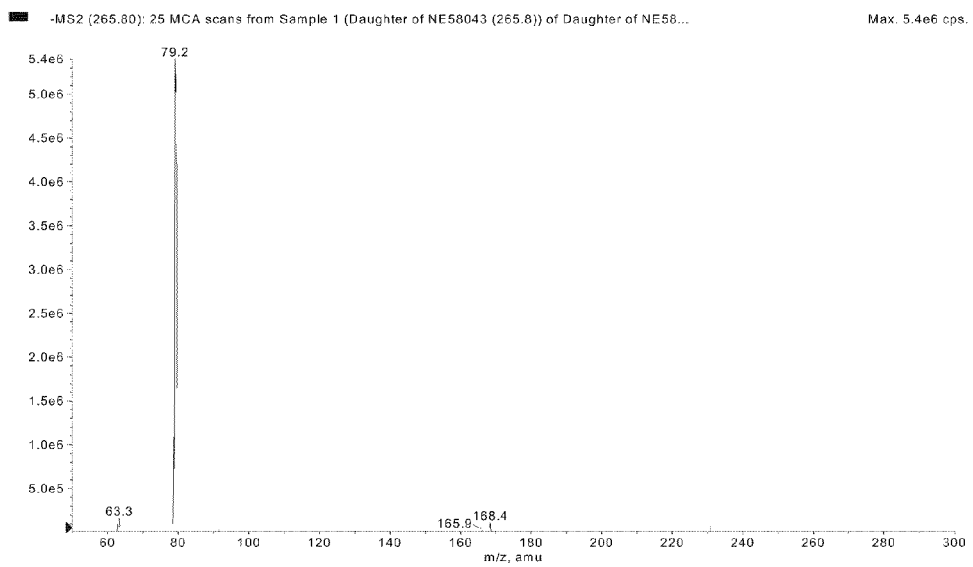
FIGURE 2. ESI-MS Spectrum of Deoxy-Risedronate

FIGURE 3. Chromatogram of Risedronate in Mouse Urine (LLOQ 10 ng/mL)
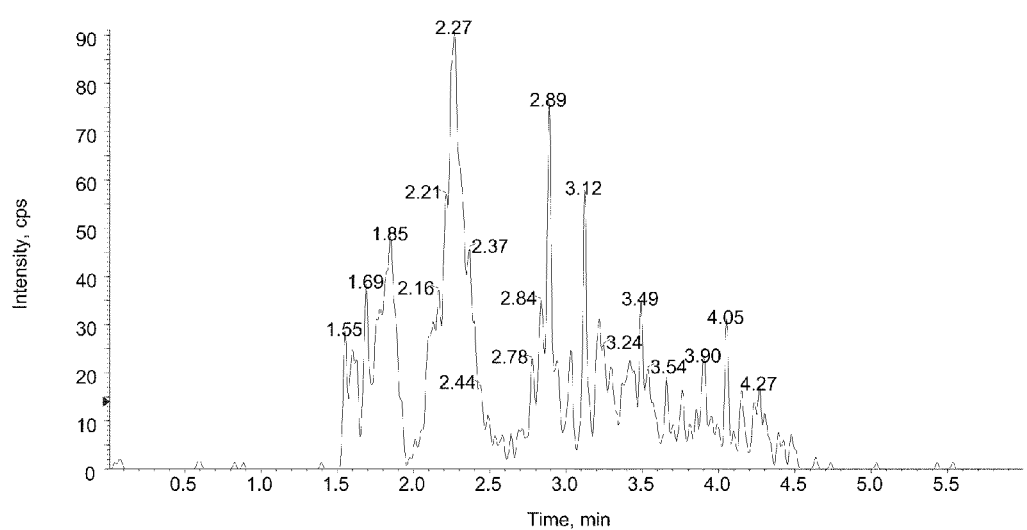

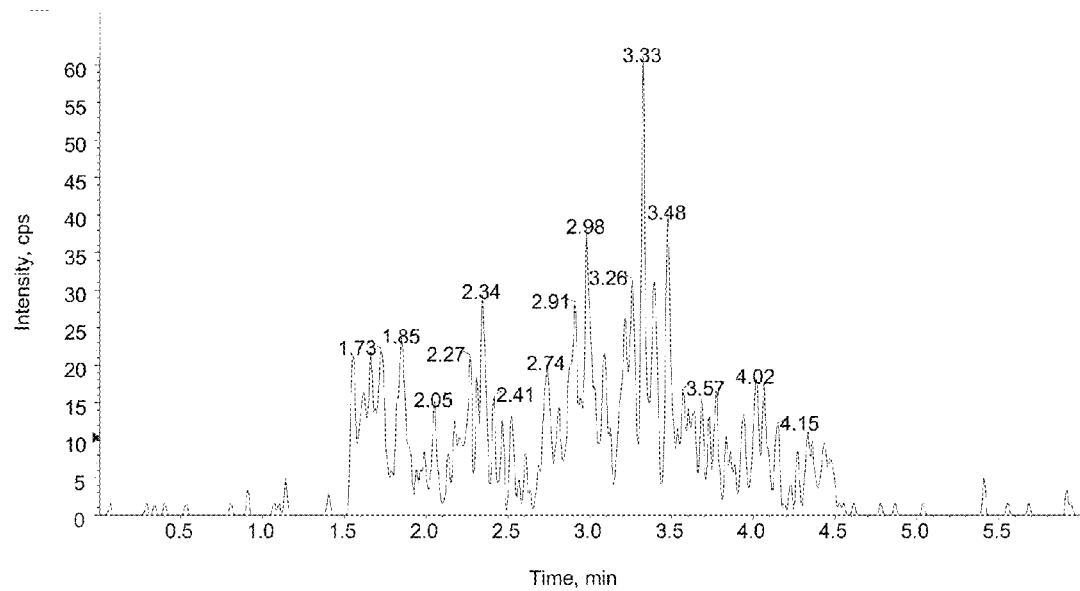
FIGURE 4. Chromatogram of Mouse Control Urine

FIGURE 5. The Typical Chromatogram of Risedronate and Deoxy-Risedronate
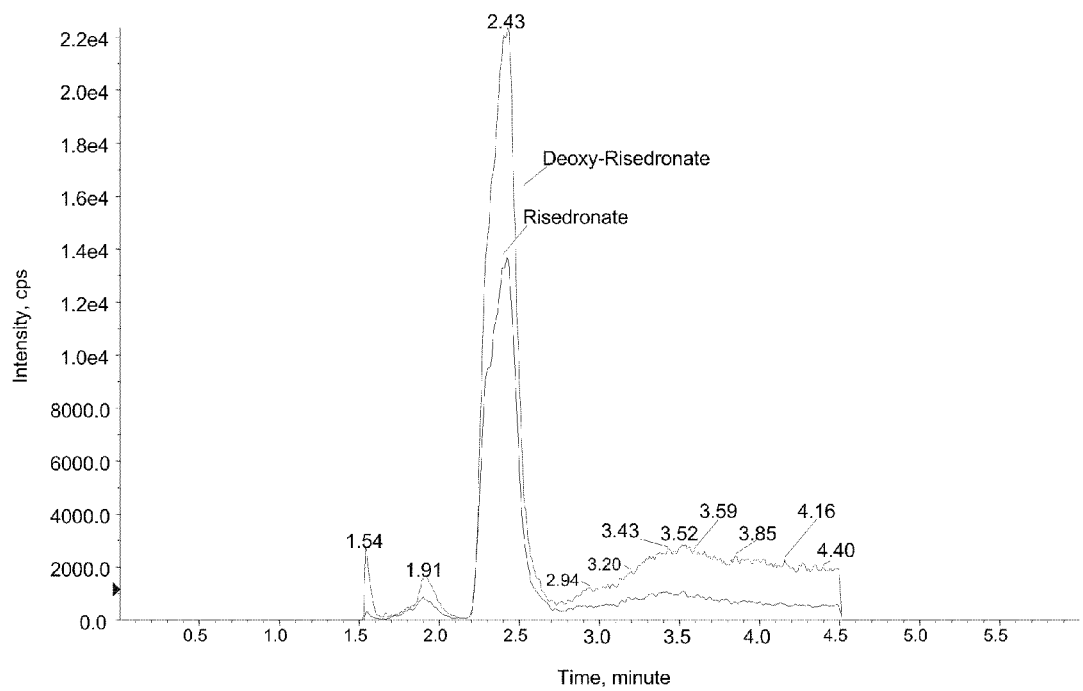

FIGURE 6. The Typical Calibration Curve of Risedronate in Mouse Urine
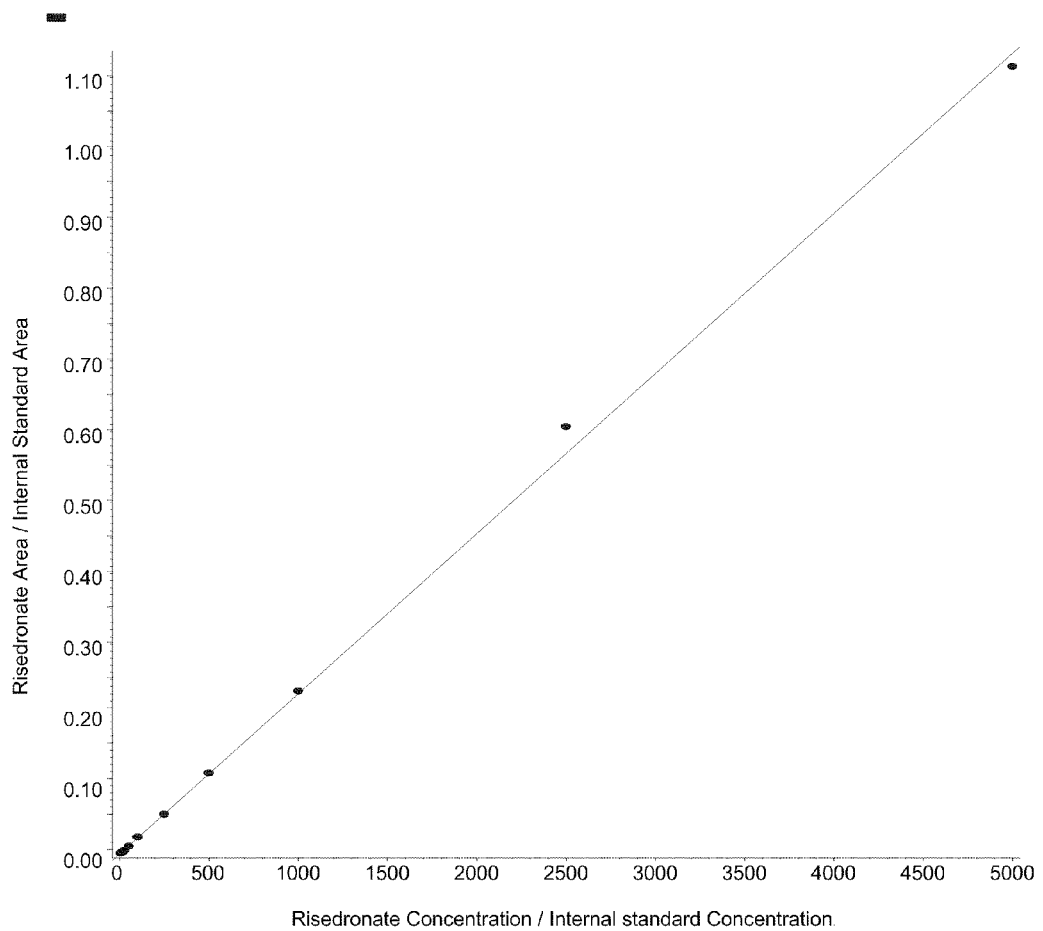

QUANTITATIVE DETERMINATION OF RISEDRONATE IN URINE BY SPE-LC-MS-MS

FIELD OF THE INVENTION

The present invention is directed to a SPE-LC-MS-MS method for quantitatively determining risedronate in a urine sample.

BACKGROUND OF THE INVENTION

Bisphosphonates inhibit bone resorption and are effective treatments for metabolic bone diseases including osteoporosis and Paget's disease (I. Elomaa, C. Blomqvist, L. Porkka, T. Holmstrom, T. Taube, C. Lamberg-Allardt, G. H. Borgstrom. *Lancet* 1985; i:1155; J. P. Kosonen, *J. Pharm Biomed Anal.* 1992; 10:881; J. A. Cantril, H. M. Buckler, D. C. Anderson, *Ann. Rheumatol. Dis.* 1986; 45:1012; H. Fleisch, *Horm. Metab. Res.* 1997; 29:145). The prevention of bone resorption results from inhibitory effects on the function of mature osteoclasts. Several bioanalytical methods have been published for bisphosphonates. In general, those methods are mainly based on ion-exchange and ion-pair chromatography with UV, fluorescence (with a pre or post column derivatization), conductivity, flame photometric phosphorus selective, refractive index and explorative light-scattering detection (V. Virtanen, L. H. J. Lajunen, *J. Chromatogr.* 1993; 617:291; V. Virtanem, L. H. J. Lajunen, *Talanta* 1993; 40: 661; S. E. Meek, D. J. Pietrzyk *Anal. Chem.* 1988; 60:1397; M. J. Lovdahl, D. J. Pietrzyk, *J. Chromatogr. A* 1999; 850:143; R. Niemi, H. Taipale, M. Ahlmark, J. Vepsalainen, T. Jarvinen, *J. Chromatogr. B* 1997; 701:97; T. L. Chester, *Anal. Chem.* 1980; 52:1621).

The technique of GC-MS, combined with acylation and silylation, has been used to determine Risedronate in human urine (D. Y. Mitchell, R. A. Eusebio, L. E. Dunlap, K. A. Pallone, J. D. Nesbitt, D. A. Russell, M. E. Clay, P. J. Bekker, *Pharm. Res.* 1998; 15:228). The more sensitive method for analysis of Risedronate in human urine has been achieved using enzyme linked immunosorbent assay (ELISA) (D. Y. Mitchell, M. A. Heise, K. A. Pallone, J. D. Nesbilt, M. E. Clay, J. D. Nesbitt, D. A. Russell, C. W. Melson, *J. Clin. Pharmacol.* 1999; 48:536). The column-switching ion-pair HPLC with UV detection has also been reported to quantify the Risedronate in human urine (P. T. Vallano, S. B. Shugars, W. F. Kline, E. J. Woolf, B. K. Matuszewski, *J. Chromatogr. B* 1003; 794:23). Although some of these methods showed a very high sensitivity, they are all very complicated and time-consuming.

Recently, more effort has been put on the development of LC/MS/MS method for risedronate with post-extraction or on cartridge derivertization (L. S. Zhu, V. N. Lapko, J. W. Lee, Y. J. Basir, C. Kafonek, R. Olsen, C. Briscoe, Rapid commun. Mass Spectrom. 2006, 20: 3421; S. Turcotte, J. Couture, F. Vallee, AAPS PharmSci Vol. 5, No. 4, Abstract M1357 (2003).

The present invention is directed to a method for quantitatively determining risedronate in a urine sample comprising:
a) adding an internal standard to the urine sample;
b) applying the urine sample to an Oasis® HLB cartridge, wherein the cartridge has been pre-conditioned with methanol;
c) washing the cartridge with about 1% (v/v) TEA in water and about 1% (v/v) formic acid in methanol;
d) eluting risedronate, at least once, with a mixture of about 60% (v/v) methanol and about 40% (v/v) water containing about 3 mM EDTA under vacuum;
e) evaporating the eluted solution and reconstituting with a mixture of 10% (v/v) methanol and 90% (v/v) 0.05 M $NH_4Ac$—$NH_4OH$ buffer to provide a sample mixture of risedronate and the internal standard; and
f) analyzing the sample mixture with a LC-MS/MS system.

The aforesaid SPE-LC-MS-MS method for quantitative determination of risedronate in a urine sample is relatively simple, sensitive, precise and accurate, and more fully discussed with the aid of the following figures and detailed description below.

BRIEF DESCRIPTION OF THE DRAWINGS

FIG. 1 is the ESI-MS Spectrum of Risedronate.

FIG. 2 is the ESI-MS Spectrum of Deoxy-risedronate.

FIG. 3 is the Chromatogram of Risedronate in Mouse Urine (LLOQ 10 ng/mL), wherein the intensity of the peak at retention of 2.27 minute is more than three times of the intensity of the same peak in the HPLC Spectrum of Blank Mouse Urine Sample. This means that the risedronate concentration at 10 ng/mL in mouse urine can be quantified.

FIG. 4 is the Chromatogram of Mouse Control Urine.

FIG. 5 is the Typical Chromatogram of Risedronate and Deoxy-Risedronate.

FIG. 6 is the Typical Calibration Curve of Risedronate in Mouse Urine.

DETAILED DESCRIPTION OF THE INVENTION

Definitions and Abbreviations

As used above, and throughout the description of the invention, the following abbreviations, unless otherwise indicated, shall be understood to have the following meanings:

amu Atom mass unit

Cps Count per second

CV % Percent coefficient of variation

Diff % Percentage difference between theoretical concentration and measured concentration EDTA Ethylenediaminetetraacetic acid ESI Electrical Spray Ionization HPLC High Pressure Liquid Chromatography LC-MS High Pressure Liquid Chromatography-Mass Spectrometry LLOQ Lower limit of quantity MRM Multiple reaction monitoring MS Mass Spectrometry m/z Mass/charge $NH_4Ac$ Ammonium acetate $NH_4OH$ Ammonium hydroxide SD Standard deviation SPE Solid phase extraction TEA Triethylamine v/v Volume/volume As used above, and throughout the description of the invention, the following terms, unless otherwise indicated, shall be understood to have the following meanings.

"Deoxy-Risedronate" means (1-phosphono-2-pyridin-3-yl-ethyl)-phosphonic acid, having the following chemical structure:

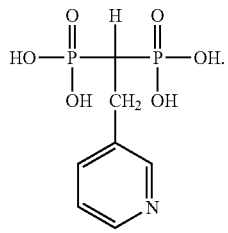

"Inertsil Phenyl-3 HPLC column" is manufactured and sold by Varian, Inc.

"Internal standard" is a chemical substance that is added in a constant amount to samples, blank and calibration standards in an analysis. This chemical substance is used for calibration by plotting the ratio of the analyte signal to the internal standard signal as a function of the analyte concentration of the standards. This is done to measure and correct for the loss of analyte during sample preparation or sample inlet. Particularly, the internal standard is a compound that has similar, but not same, chemical structure to the analyte.

Oasis® HLB cartridge" is manufactured and sold by Waters Corporation. The size of the cartridge is dependent upon the risedronate concentration in the urine sample. The lower risedronate concentration the urine sample has, the bigger size of the cartridge, and the larger volume of urine sample and the solution to wash the cartridge and elute risedronate should be used.

"Risedronate" means (1-hydroxy-1-phosphono-2-pyridin-3-yl-ethyl)-phosphonic acid, having the following chemical structure:

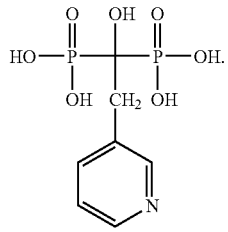

"Urine sample" means mammalian urine sample, including human urine sample.

Particular Embodiment of the Invention

One particular embodiment of the invention is the method for quantitatively determining risedronate in a urine sample, wherein the urine sample is a mouse or rat urine sample.

Another particular embodiment of the invention is the method for quantitatively determining risedronate in a urine sample, wherein the internal standard is deoxy-risedronate.

Another particular embodiment of the invention is the method for quantitatively determining risedronate in a urine sample, wherein the Oasis® HLB cartridge is a 30 mg Oasis® HLB cartridge.

Another particular embodiment of the invention is the method for quantitatively determining risedronate in a urine sample, wherein the internal standard is deoxy-risedronate that is added as a solution in water; more particularly as an about 10 μg/mL solution in water.

Another particular embodiment of the invention is the method for quantitatively determining risedronate in a urine sample, wherein the amount of the urine sample is about 0.4 mL.

Another particular embodiment of the invention is the method for quantitatively determining risedronate in a urine sample, wherein the cartridge has been pre-conditioned with about 1 mL of methanol.

Another particular embodiment of the invention is the method for quantitatively determining risedronate in a urine sample, wherein the cartridge has been pre-conditioned with about 1 mL of methanol and followed by about 0.5 mL of 1% (v/v) TEA in water.

Another particular embodiment of the invention is the method for quantitatively determining risedronate in a urine sample, wherein the cartridge is washed with about 0.5 mL of about 1% (v/v) TEA in water and about 0.5 mL of about 1% (v/v) formic acid in methanol.

Another particular embodiment of the invention is the method for quantitatively determining risedronate in a urine sample, wherein the amount of the mixture of about 60% (v/v) methanol and about 40% (v/v) water containing about 3 mM EDTA is about 1.5 mL.

Another particular embodiment of the invention is the method for quantitatively determining risedronate in a urine sample, wherein risedronate is eluted twice with about 0.75 mL of the mixture of about 60% (v/v) methanol and about 40% (v/v) water containing about 3 mM EDTA.

Another particular embodiment of the invention is the method for quantitatively determining risedronate in a urine sample, wherein the amount of the mixture of 10% (v/v) methanol and 90% (v/v) 0.05 M $NH_4Ac$—$NH_4OH$ buffer is about 100 μL.

Another particular embodiment of the invention is the method for quantitatively determining risedronate in a urine sample, wherein the internal standard is deoxy-risedronate, and analyzing the sample mixture with a LC-MS/MS system comprises separating risedroante and deoxy-risedronate by HPLC on an Inertsil Phenyl-3 HPLC column by gradient elution with a mixture of solution A and solution B, wherein the amount of solution A is increased from about 10% (v/v) to about 95% (v/v), and wherein the solution A is about 90% (v/v) methanol in water, and solution B is about 10 mM ammonium acetate-acetic acid buffer with 2% (v/v) triethylamine.

Another particular embodiment of the invention is the method for quantitatively determining risedronate in a mouse or rat urine sample, comprising:
a) adding about 100 μL of about 10 μg/mL dexoy-risedronate solution in water to about 0.4 mL of the mouse or rat urine sample;
b) applying the mouse or rat urine sample to a 30 mg Oasis® HLB cartridge, wherein the cartridge has been pre-conditioned with about 1 mL of methanol and followed by about 0.5 mL of 1% (v/v) TEA in water;
c) washing the cartridge with about 0.5 mL of 1% (v/v) TEA in water and about 0.5 mL of 1% (v/v) formic acid in methanol;
d) eluting risedronate with about 1.5 mL of a mixture of about 60% (v/v) methanol and about 40% (v/v) water containing about 3 mM EDTA under vacuum;
e) evaporating the eluted solution and reconstituting with about 100 μL of a mixture of about 10% (v/v) of methanol and about 90% (v/v) of about 0.05 M $NH_4Ac$—$NH_4OH$ buffer to provide a sample mixture of risedronate and dexoy-risedronate; and f) analyzing the sample mixture with a LC-MS/MS system, wherein risedronate and dexoy-risedronate are separated by HPLC on an Inertsil Phenyl-3 HPLC column by gradient elution with a mixture of solution A and solution B, wherein the amount of solution A is increased from about 10% (v/v) to about 95% (v/v), and wherein the solution A is about 90% (v/v) methanol in water, and solution B is about 10 mM ammonium acetate-acetic acid buffer with 2% (v/v) triethylamine. Another particular embodiment of the invention is the method for quantitatively determining risedronate in a mouse or rat urine sample, comprising:

a) adding about 100 μL of about 10 μg/mL dexoy-risedronate solution in water to about 0.4 mL of the mouse or rat urine sample;
b) applying the mouse or rat urine sample to a 30 mg Oasis® HLB cartridge, wherein the cartridge has been pre-conditioned with about 1 mL of methanol and followed by about 0.5 mL of 1% (v/v) TEA in water;
c) washing the cartridge with about 0.5 mL of 1% (v/v) TEA in water and about 0.5 mL of 1% (v/v) formic acid in methanol;
d) eluting risedronate twice with about 0.75 mL of a mixture of about 60% (v/v) methanol and about 40% (v/v) water containing about 3 mM EDTA under vacuum;
e) evaporating the eluted solution and reconstituting with about 100 μL of a mixture of about 10% (v/v) of methanol and about 90% (v/v) of about 0.05 M $NH_4Ac$—$NH_4OH$ buffer to provide a sample mixture of risedronate and dexoy-risedronate; and
f) analyzing the sample mixture with a LC-MS/MS system, wherein risedronate and dexoy-risedronate are separated by HPLC on an Inertsil Phenyl-3 HPLC column by gradient elution with a mixture of solution A and solution B, wherein the amount of solution A is increased from about 10% (v/v) to about 95% (v/v), and wherein the solution A is about 90% (v/v) methanol in water, and solution B is about 10 mM ammonium acetate-acetic acid buffer with 2% (v/v) triethylamine.

It is to be understood that this invention covers all appropriate combinations of the particular embodiments referred thereto.

The present invention will appear more clearly from the following example that is presented as an illustration only and is not to be considered as limiting the invention in its scope.

EXAMPLE

Step 1: Preparation of Risedronate Urine Standards in Mouse or Rat Urine

A 1 mg/mL risedronate stock solution is prepared by dissolving risedronate in HPCL grade water. 250 μg/mL, 100 μg/mL and 50 μg/mL risedronate standard solutions are prepared by diluting 250 μL, 100 μL and 50 μL of the 1 mg/mL risedronate stock solution to 1 mL with HPLC grade water, respectively. Appropriate dilutions of 250 μg/mL, 100 μg/mL and 50 μg/mL risedronate standard solutions are performed to yield risedronate working solutions of 25 μg/mL, 10 μg/mL, 5 μg/mL, 2.5 μg/mL and 1 μg/mL. Riseronate urine standards, ranging from 10 ng/mL to 2500 ng/mL, are prepared by adding 4 μL of each working solution into 0.4 mL of mouse or rat control urine (i.e., urine from mouse or rat that is not dosed with risedronate).

Step 2: Sample Preparation

A 0.4 mL urine sample collected from mouse or rat that has been dosed with risedronate is transferred to a 10×75 mm glass culture tube. 100 μL of stock internal standard solution, i.e., 10 μg/mL deoxy-risedronate solution in water, and 100 μL of 5% TEA in water are added to all the risedronate urine standards and the urine sample, respectively.

Sample extraction is performed with a 30 mg Oasis® HLB cartridge (1 mL, manufactured and sold by Waters Corporation, Catalog No.: WAT094225). The cartridges are conditioned with 1 mL methanol and followed by 0.5 mL of 1% TEA in water. The urine sample is applied to the cartridge. The cartridge is washed with 0.5 mL of 1% TEA in water and 0.5 mL of 1% formic acid in methanol, and then the analyte and the internal standard are eluted using two consecutive elution steps with 0.75 mL of a mixture of 60% methanol in water containing 3 mM EDTA. During the samples extraction, a vacuum (5-15 Psi) is used at each step to pull the liquid through the cartridges. The eluted solution is dried under nitrogen at 37° C. for 70 minutes and then the residue is reconstituted in 100 μL of 10% methanol/90% 0.05 M $NH_4Ac$—$NH_4OH$ buffer (pH 9.26).

Step 3: LC-MS/MS Analysis

The analysis of Risedronate is performed using API 4000 LC-MS/MS system (sold by MDS Sciex), including a Shimadzu LC-10AD pump, SCL-10A VP system controller, Leap Technologies HTS PAL autosampler and API 4000 triple quadrupole mass-spectrometer.

Risedronate and the internal standard are separated on an Inertsil Phenyl-3 HPLC column (3 μL, 50×030 mm, manufactured and sold by Varian, Inc., Catalog No.: 0408-050x030) by gradient elution with a mixture of solution A and solution B in 6 minutes, wherein the amount of solution A is increased from 10% to 95%. The solution A is 90% methanol in water, and the solution B is 10 mM ammonium acetate-acetic acid buffer (pH=5.0) with 2% triethylamine. The flow rate is kept constant at 0.2 mL/min. The sample (10 μL reconstitute) is injected onto the HPLC column directly. The mass spectrometer is programmed to monitor the transition m/z 281.9→63.1 for risedronate under negative mode with a collision energy of −58 volts. The m/z 265.8→79.2 is used to measure deoxy-Risedronate internal standard. The source temperature is set at 350° C. An analytical run time of 6 minutes is employed.

Results

Linearity

The assay for risedronate mouse or rat urine standard is linear from 10 to 2500 ng/mL with an LLOQ of 10 ng/mL. The determined accuracy at LLOQ is 14.8% with a precision of 17.8% (n=3). The regression parameters obtained during the validation are reported in table 1. Correlation coefficients of 0.98 or greater for risedronate are obtained from the day-to-day analysis. A typical calibration curve is represented in FIG. 6.

TABLE 1

Regression parameters for risedronate in mouse urine

| Curve No/Date | Regression Parameters | | |
|---|---|---|---|
| | Slope (response/concentration) | Intercept (response at concentration 0) | Correlation Coefficient |
| | Within-day | | |
| #1 | 0.000260 | 0.00208 | 0.9993 |
| #2 | 0.000257 | 0.00151 | 0.9961 |

TABLE 1-continued

Regression parameters for risedronate in mouse urine

| Curve No/Date | Regression Parameters | | |
|---|---|---|---|
| | Slope (response/ concentration) | Intercept (response at concentration 0) | Correlation Coefficient |
| #3 | 0.000232 | 0.00300 | 0.9895 |
| Mean | 0.000250 | 0.00220 | 0.9950 |
| SD | 0.000015 | | |
| CV % | 6.2 | | | levels ranged from 5.2 to 10.3%. The within-day and the day-to-day precisions for the standards ranged from 0.3 to 26%.

Accuracy

The assay accuracy is expressed as the percent difference between the mean determined quality control concentration and the theoretical value.

The within-day assay accuracy for the mouse urine controls ranged from −5.3 to 4.4%. The day-to-day accuracy is determined over three analysis days using the controls at 3 concentration levels. The day-to-day accuracy ranged from −4.0 to 6.0%. The accuracy from the back-calculated concentrations of the mouse urine standards is within ±15%.

TABLE 2

The accuracy and precision of mouse urine calibration standards of risedronate

| Replicate Or date | Nominal Concentration (ng/mL) | | | | | | | |
|---|---|---|---|---|---|---|---|---|
| | 10 | 25 | 50 | 100 | 250 | 500 | 1000 | 2500 |
| Within-day | | | | | | | | |
| #1 | 7.93 | 20.7 | 49.4 | 100 | 237 | 422 | 995 | 2460 |
| #2 | 13.3 | 22 | 42.8 | 91.6 | 238 | 388 | 868 | 2470 |
| #3 | 9.94 | 25.4 | 50.6 | 97 | 253 | 476 | 976 | 2500 |
| Mean | 10.39 | 22.7 | 47.6 | 96.2 | 243 | 429 | 946 | 2477 |
| SD | 2.71 | 2.43 | 4.20 | 4.26 | 8.96 | 44.38 | 68.50 | 20.82 |
| CV % | 26.1 | 10.7 | 8.8 | 4.4 | 3.7 | 10.4 | 7.2 | 0.8 |
| Diff % | 3.9 | −9.2 | −4.8 | −3.8 | −2.9 | −14.3 | −5.4 | −0.9 |
| Day-to-day | | | | | | | | |
| Day 1 | 13.8 | 24.7 | 46.9 | 93.5 | 237 | 532 | 1120 | 2610 |
| Day 2 | 10.7 | 21.5 | 50.6 | 107 | 248 | 501 | 1010 | 2640 |
| Day 3 | 9.94 | 25.4 | 50.6 | 97 | 253 | 476 | 976 | 2500 |
| Mean | 11.48 | 23.9 | 49.4 | 99.2 | 246 | 503 | 1035 | 2583 |
| SD | 2.04 | 2.08 | 2.14 | 7.01 | 8.19 | 28.05 | 75.27 | 73.71 |
| CV % | 17.8 | 8.7 | 4.3 | 7.1 | 3.3 | 5.6 | 7.3 | 2.9 |
| Diff % | 14.8 | −4.5 | −1.3 | −0.8 | −1.6 | 0.6 | 3.5 | 3.3 |

TABLE 1-continued

Regression parameters for risedronate in mouse urine

| Curve No/Date | Regression Parameters | | |
|---|---|---|---|
| | Slope (response/ concentration) | Intercept (response at concentration 0) | Correlation Coefficient |
| Day-to-day | | | |
| Day 1 | 0.000267 | 0.00331 | 0.997 |
| Day 2 | 0.000229 | 0.000594 | 0.9974 |
| Day 3 | 0.000260 | 0.00208 | 0.9993 |
| Mean | 0.000252 | 0.00199 | 0.9979 |
| SD | 0.000020 | | |
| CV % | 8.0 | | |

Specificity

A small peak, at retention time of 2.27, is found in mouse control urine, but the peak height of LLOQ (10 ng/mL) is more than three times of the intensity of the peak in the mouse control urine (see FIG. 3 and FIG. 4). Thus, risedronate concentration at 10 ng/mL can be quantified.

Precision

Precision is expressed as the percent coefficient of variation of the concentrations measured at each control level over the duration of the study. The within-day coefficient of variation for the controls in mouse urine ranged from 2.2 to 9.6%. The day-to-day precision for the controls at 3 concentration

TABLE 3

The accuracy and precision of mouse urine quality controls of risedronate

| Date | Nominal Concentration (ng/mL) | | |
|---|---|---|---|
| | 25 | 250 | 2500 |
| Day 1 | 28.2 | 257 | 2900 |
| | 30 | 290 | 2580 |
| | 26.1 | 236 | 2870 |
| Day 2 | 28.9 | 226 | 2650 |
| | 27.2 | 208 | 2800 |
| | 25.5 | 238 | 2470 |
| Day 3 | 27.1 | 244 | 2650 |
| | 24.1 | 246 | 2670 |
| | 24.4 | 231 | 2520 |
| | 23.8 | 204 | 2600 |
| | 20.6 | 259 | 2610 |
| Within-day (Day 3) | | | |
| Mean | 24.0 | 237 | 2610 |
| SD | 2.31 | 20.8 | 57.9 |
| CV % | 9.6 | 8.8 | 2.2 |
| Diff % | −4 | −5.28 | 4.4 |
| Day-to-day | | | |
| Mean | 26.0 | 240 | 2665 |
| SD | 2.69 | 24.1 | 138 |
| CV % | 10.3 | 10.1 | 5.2 |
| Diff % | 4.0 | −4.0 | 6.6 |

Recovery

A recovery of risedronate in extracted mouse urine as compared to extracted mouse urine blank with neat spiked is around 51.3%

TABLE 4

Recovery of risedronate from mouse urine samples (250 ng/mL)

| Replicates | Extracted Urine Sample (peak area) | Extracted Blank Urine Sample + spiked neat peak area |
|---|---|---|
| #1 | 12400 | 30400 |
| #2 | 18000 | 28800 |
| #3 | 16600 | 29800 |
| #4 | 18100 | 36000 |
| #5 | 14500 | 30300 |
| Mean | 15920 | 31060 |
| SD | 2447 | 2833 |
| CV % | 15.4 | 9.1 |
| Recovery (%) | 51.3 | |

The present invention may be embodied in other specific forms without departing from the spirit or essential attributes thereof.

We claim:

1. A method for quantitatively determining risedronate in a mouse or rat urine sample, comprising:
   a) adding about 100 μL of about 10 μg/mL dexoy-risedronate solution in water to about 0.4 mL of the mouse or rat urine sample;
   b) applying the mouse or rat urine sample to a 30 mg Oasis® HLB cartridge, wherein the cartridge has been pre-conditioned with about 1 mL of methanol and followed by about 0.5 mL of 1% (v/v) TEA in water;
   c) washing the cartridge with about 0.5 mL of 1% (v/v) TEA in water and about 0.5 mL of 1% (v/v) formic acid in methanol;
   d) eluting risedronate with about 1.5 mL of a mixture of about 60% (v/v) methanol and about 40% (v/v) water containing about 3 mM EDTA;
   e) evaporating the eluted solution and reconstituting with about 100 μL of a mixture of about 10% (v/v) of methanol and about 90% (v/v) of about 0.05 M $NH_4Ac$—$NH_4OH$ buffer to provide a sample mixture of risedronate and dexoy-risedronate; and
   f) analyzing the sample mixture with a LC-MS/MS system, wherein risedronate and dexoy-risedronate are separated by HPLC on an Inertsil Phenyl-3 HPLC column by gradient elution with a mixture of solution A and solution B, wherein the amount of solution A is increased from about 10% (v/v) to about 95% (v/v), and wherein the solution A is about 90% (v/v) methanol in water, and solution B is about 10 mM ammonium acetate-acetic acid buffer with 2% (v/v) triethylamine.

2. A method for quantitatively determining risedronate in a mouse or rat urine sample, comprising:
   a) adding about 100 μL of about 10 μg/mL dexoy-risedronate solution in water to about 0.4 mL of the mouse or rat urine sample;
   b) applying the mouse or rat urine sample to a 30 mg Oasis® HLB cartridge, wherein the cartridge has been pre-conditioned with about 1 mL of methanol and followed by about 0.5 mL of 1% (v/v) TEA in water;
   c) washing the cartridge with about 0.5 mL of 1% (v/v) TEA in water and about 0.5 mL of 1% (v/v) formic acid in methanol;
   d) eluting risedronate twice with about 0.75 mL of a mixture of about 60% (v/v) methanol and about 40% (v/v) water containing about 3 mM EDTA;
   e) evaporating the eluted solution and reconstituting with about 100 μL of a mixture of about 10% (v/v) of methanol and about 90% (v/v) of about 0.05 M $NH_4Ac$—$NH_4OH$ buffer to provide a sample mixture of risedronate and dexoy-risedronate; and
   f) analyzing the sample mixture with a LC-MS/MS system, wherein risedronate and dexoy-risedronate are separated by HPLC on an Inertsil Phenyl-3 HPLC column by gradient elution with a mixture of solution A and solution B, wherein the amount of solution A is increased from about 10% (v/v) to about 95% (v/v), and wherein the solution A is about 90% (v/v) methanol in water, and solution B is about 10 mM ammonium acetate-acetic acid buffer with 2% (v/v) triethylamine.

* * * * *